US00PP25987P2

(12) United States Plant Patent
Ault

(10) Patent No.: US PP25,987 P2
(45) Date of Patent: Oct. 13, 2015

(54) ***BAPTISIA* PLANT NAMED 'MOJITO'**

(50) Latin Name: ***Baptisia* hybrid**
Varietal Denomination: Mojito

(71) Applicant: James Robert Ault, Libertyville, IL (US)

(72) Inventor: James Robert Ault, Libertyville, IL (US)

(73) Assignee: CHICAGO LAND GROWS, INC., Glencoe, IL (US)

( * ) Notice: Subject to any disclaimer, the term of this patent is extended or adjusted under 35 U.S.C. 154(b) by 80 days.

(21) Appl. No.: 13/999,434

(22) Filed: Feb. 25, 2014

(51) Int. Cl.
*A01H 5/00* (2006.01)

(52) U.S. Cl.
USPC ..... Plt./263.1

(58) Field of Classification Search
USPC ..... Plt./263.1, 226
See application file for complete search history.

*Primary Examiner* — Annette Para
(74) *Attorney, Agent, or Firm* — Penny J. Aguirre

(57) ABSTRACT

A new cultivar of interspecific *Baptisia*, 'Mojito', that is characterized by its flowers that are light yellow-green in color, its flowers that are borne very densely on the raceme, its inflorescences that are borne upright and within the foliage, its foliage that is deep yellow-green in color, its stems that do not lodge, and its early and extended four-week long bloom period that begins in early May in northern Illinois.

2 Drawing Sheets

Botanical classification: *Baptisia* hybrid.

Cultivar designation: 'Mojito'.

The present invention relates to a new and distinct cultivar of *Baptisia* plant of hybrid origin, botanically known as *Baptisia* 'Mojito' and will be referred to hereafter by its cultivar name, 'Mojito'. The new cultivar represents a new false indigo, an herbaceous perennial grown for landscape use.

The new invention arose from an ongoing breeding program in a dedicated test plot in Glencoe, Ill. The objective of the breeding program is to develop novel interspecific hybrids of *Baptisia* that exhibit unique flower coloration, hybrid vigor, ease of clonal propagation, and desirable plant habits.

'Mojito' was selected as a single unique plant by the Inventor in June of 2008 after evaluating seedlings that derived from a cross made in May of 2004 between unnamed plants of hybrid *Baptisia* from the Inventor's breeding program. The female parent was a seedling that derived from open pollination of an interspecific hybrid *Baptisia* (*australis*×*leucophaea*). The male parent was a seedling that derived from open pollination of an interspecific hybrid *Baptisia* (*australis*×*sphaerocarpa*).

Asexual propagation of the new cultivar was first accomplished by stem tip cuttings under the direction of the Inventor in July of 2009 in Glencoe, Ill. Asexual propagation by stem shoot tip cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Mojito' as a unique cultivar of *Baptisia*.

1. 'Mojito' exhibits flowers that are light yellow-green in color.
2. 'Mojito' exhibits flowers that are borne very densely on the raceme.

3. 'Mojito' exhibits inflorescences that are borne upright and within the foliage.
4. 'Mojito' exhibits foliage that is deep yellow-green in color.
5. 'Mojito' exhibits stems that do not lodge.
6. 'Mojito' exhibits an early and extended four-week long bloom period that begins in early May in northern Illinois.

The female parent of 'Mojito' differs from 'Mojito' in having flowers that are cream colored with a hint of yellow, in having flowering stems that are held clear above the foliage, and in having stems the occasionally lodge. The male parent differs from 'Mojito' in having flowers that are cream colored with a hint of butter yellow, in having a conspicuously back-swept banner petal, and in having a bloom period that begins two weeks later. 'Mojito' can be most closely compared to the *Baptisia* cultivar 'Starlite' (U.S. Plant Pat. No. 19,971) and typical plants of *Baptisia bracteata* (syn. *B. leucophaea*). 'Starlite' is similar to 'Mojito' in having an early bloom period starting in early May in northern Illinois and in being very floriferous. 'Starlite' differs from 'Mojito' in having flowers that are lavender to blue in color with a yellow keel, in having inflorescences that are upright to leaning in aspect, and in having flowers that are borne less densely on the raceme. Typical plants of *Baptisia bracteata* are similar to 'Mojito' in having an early bloom period starting in early May in northern Illinois. Typical plants of *Baptisia bracteata* differ from 'Mojito' in having flowers that are cream colored with hints of lemon yellow, in having conspicuously pubescent stems and foliage, in having horizontal inflorescences, in having flowers that are produced on only one side of the inflorescences.

BRIEF DESCRIPTION OF THE DRAWINGS

The accompanying colored photographs illustrate the overall appearance and distinct characteristics of the new *Baptisia*. The photographs in FIG. 1 and FIG. 2 were taken of a plant five years in age and the photograph in FIG. 3 was taken of a plant nine years in age, both plants were grown outdoors in a trial plot in Glencoe, Ill.

The photograph in FIG. 1 provides a close-up view of an inflorescence of 'Mojito'.

Figure 1:
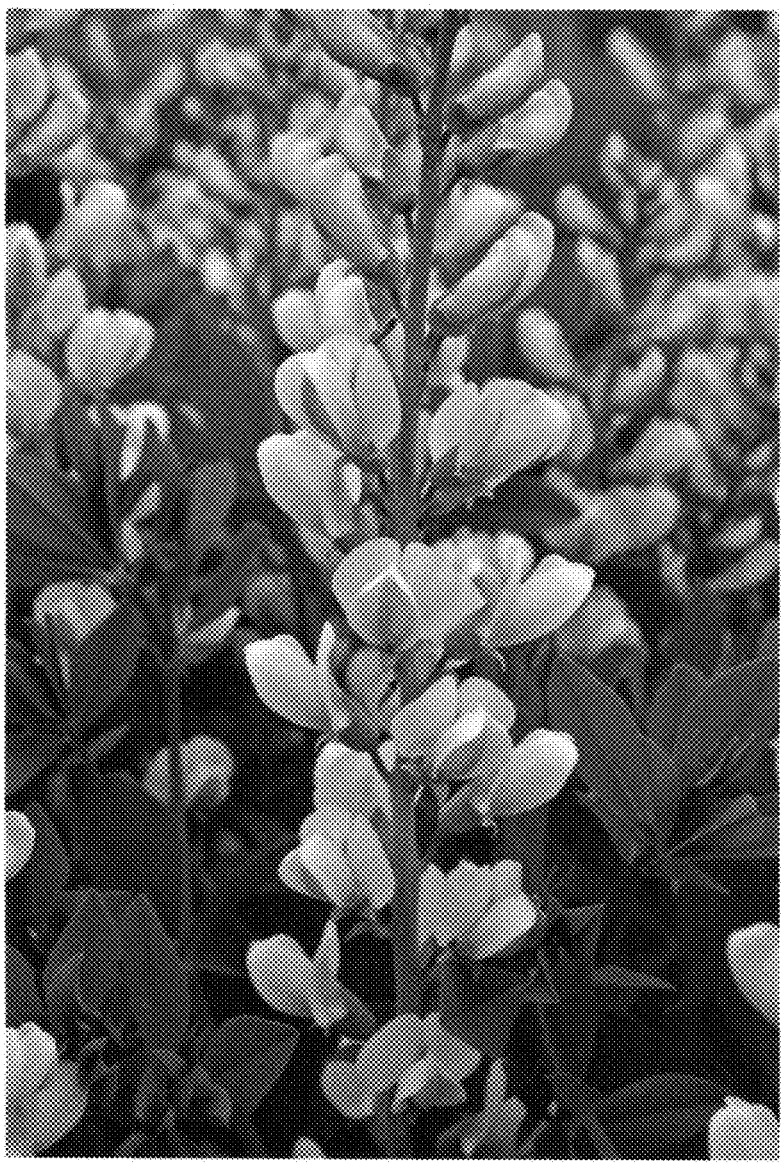
Figure 2:
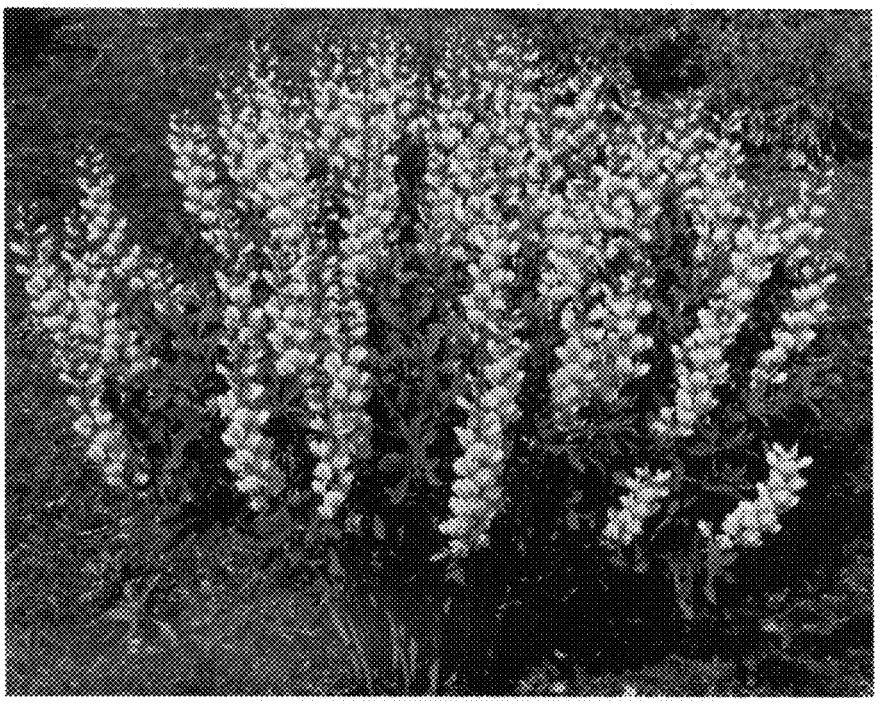

The photograph in FIG. 2 provides a side view of 'Mojito' in bloom and illustrates the plant habit and flowering habit.

Figure 3:
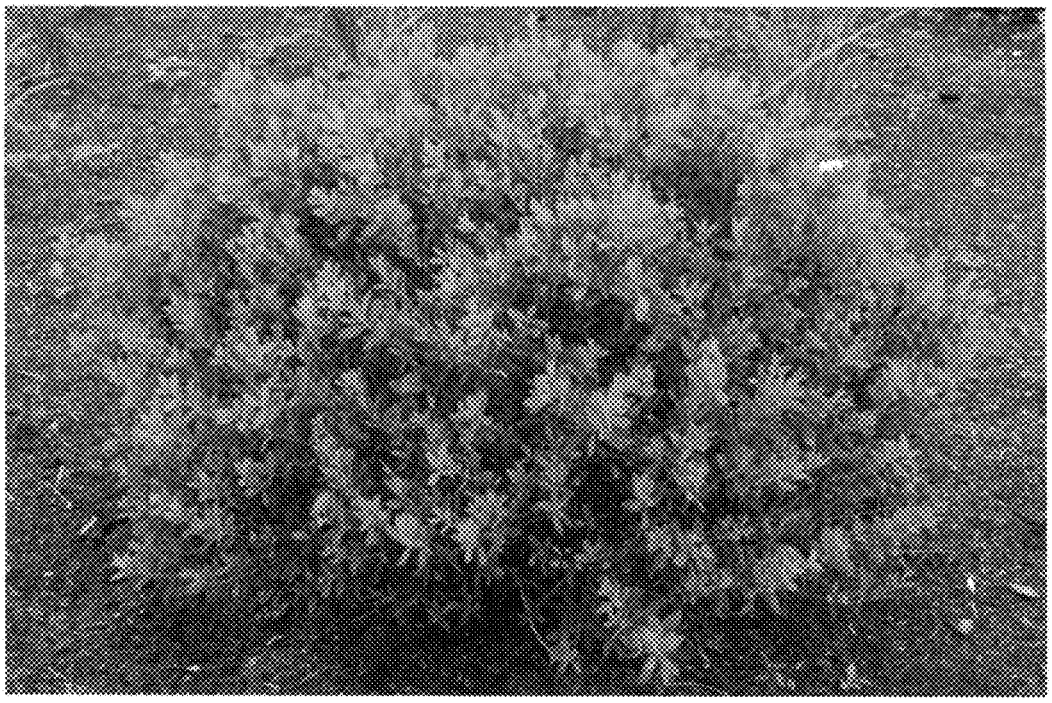

The photograph in FIG. 3 provides a side view of the late summer foliage of 'Mojito'.

The colors in the photographs are as close as possible with the photographic and printing technology utilized and the color values cited in the detailed botanical description accurately describe the colors of the new *Baptisia*.

DETAILED BOTANICAL DESCRIPTION OF THE PLANT

The following is a detailed description of five year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Four weeks from early May to early June in northern Illinois.

*Plant habit*.—Upright with a dense, spreading mound of foliage.

*Height and spread*.—Reaches 1.1 m in width and 1.5 m in height.

*Hardiness*.—U.S.D.A. Zones 4 to 8.

*Diseases and pests*.—No susceptibility to diseases or pests has been observed.

*Root description*.—Fine and fibrous.

Growth and propagation:

*Propagation*.—Rooting of stem tip cuttings.

*Growth rate*.—Vigorous.

Stem description:

*Branch habit*.—Densely branched; seven stems on a three year old plant, 29 stems on a five year old plant, and 60 stems on a seven year old plant; with an average of 3 secondary branches, and 0 to 1 tertiary branches per secondary branch.

*Stem size*.—Main stem; average of 75 cm (including peduncle) in length and 8 mm in width, secondary; average of 21 cm in length and 4 mm, tertiary; an average of 8 cm in length and 2 mm in width.

*Stem shape*.—Oval.

*Stem color*.—144B to 144C.

*Stem surface*.—Glabrous, satiny and slightly glaucous with slight vertical ridges.

Foliage description:

*Leaf shape*.—Fan-shaped in overall outline.

*Leaf division*.—3-palmate.

*Leaf internode*.—Foliage begins about 22 cm from base, an average of 8 cm on main stem and an average of 5 cm on secondary branches.

*Leaf size*.—Average of 6 cm in length and width when mature.

*Leaf quantity*.—Average of 19 per stem.

*Leaflet shape*.—Oblanceolate.

*Leaflet base*.—Cuneate.

*Leaflet apex*.—Acute.

*Leaflet venation*.—Pinnate pattern, not conspicuous, color matches leaflet color on the upper and lower surface with the mid rib of lower surface 138C.

*Leaflet margins*.—Entire.

*Leaf attachment*.—Petiolate.

*Leaf arrangement*.—Alternate.

*Leaflet surface*.—Glabrous and slightly glaucous on upper and lower surface.

*Leaflet color*.—Newly expanded and mature upper and lower surface 137A, newly expanded and mature 137B.

*Leaflet size*.—Average of 5 cm in length and 1.4 cm in width.

*Petioles*.—Average of 5 mm in length and 2 mm in width, clasping to stem at mature nodes, 138B in color, surface is glabrous and satiny.

*Stipules*.—Lanceolate in shape, base is truncate to stem, apex is narrowly acute to acuminate, up to 2.3 cm in length and 7 mm in width on mature leaves, 137A in color on upper and lower surface.

Flower description:

*Inflorescence type*.—Terminal racemes of pea-like flowers on main and secondary branches, blooms from the base to the apex, flowers radially and uniformly dispersed around the inflorescences.

*Inflorescence size*.—Average of 32 cm in length and 5.5 cm in width.

*Lastingness of inflorescence*.—About 20 days.

*Flower size*.—Average of 2.5 cm in depth and about 1.7 cm in diameter.

*Flower fragrance*.—Faint.

*Flower number per inflorescence*.—Average of 39.

*Peduncle*.—Oval in shape, up to 34 cm in length and an average of 4 mm in width, 144C in color, surface is glabrous, satiny and slightly glaucous with ridges, flower internode length averages 1 cm.

*Petiole*.—Average of 5 mm in length, about 1.5 mm in width, oval in shape, 144B in color, glabrous and satiny surface.

*Flower buds*.—Kidney-shaped, about 2.5 cm in length and 1.3 cm in width, petal portion is 4D in color, calyx portion same as open flowers.

*Flower type*.—Papilionaceous, held at about a 45° angle.

*Calyx*.—Campanulate, about 9 mm in length and 5 mm in diameter, surface is glabrous and satiny, 144C in color, persistent.

*Sepals*.—5, fused with the exception of apex of each, free portion is triangular in shape 5 mm in width and 4 mm in depth with an acute apex, 144C in color.

*Corolla features*.—Papilionaceous (4 segments) with a banner, 2 lateral and a concealed keel, lateral wings; oblong in shape, about 2.3 cm in length and 9 mm in width, color on outer surface and the inner surface is 4D, rounded apex, oblique base keel; not visible visible, comprised of 2 segments surrounding reproductive organs, oblong (slightly oblique) in shape with rounded apex and oblique base, 2 cm in length and 1 cm in width, upper surface and lower surfaces are a blend of 4D and 145C in color, segments joined at center point, banner; orbicular in shape, slightly reflexed to flat, about 1.8 cm in length and width, upper and lower surface 4D with mid region and base of 145B, apex is rounded with a single notch, surface is glabrous on all sections.

*Receptacle*.—Disk-shaped, gelatinous, 144B in color, about 4 mm in diameter and 2 mm in depth.

Reproductive organs:

*Gynoecium*.—1 Pistil, about 2.3 cm in length, 1.5 mm in width; style is 144C in color and 1 cm in length; stigma minute, too small to read color, ovary is superior with a stipe, 144A in color, 6 mm in length and 2 mm in width and slightly pubescent; stipe is 144C in color, 3 mm in length and 1 mm in width.

*Androcoecium*.—10 stamens, not united, 2 cm in length and 1 mm in width; filament is 1.9 cm in length, 1 mm in width and 145C in color; anther is dorsifixed, 2 mm in length and 1 mm in width and 165B in color, pollen is abundant in quantity and 13C in color.

*Fruit*.—An inflated pod, technically a legume, average of 1 produced per inflorescence (open-pollinated), elliptic-oblong in shape, average of 3 cm in length by 1.5 cm in width with a beak approx. 1.5 cm in length, color of outer surface when mature is a blend of N200A and 200A, color of inner surface N199B, walls 1.5 mm and hard at maturity, seed; average of 7 per fruit (open-pollinated), 200B in color, oval with the hilum side more or less straight, seed compressed to flattish, 4 mm in length, 3 mm in width and 2 mm in thickness.

It is claimed:

1. A new and distinct cultivar of *Baptisia* plant named 'Mojito' as herein illustrated and described.

* * * * *